US006432992B1

(12) United States Patent
Aubourg et al.

(10) Patent No.: US 6,432,992 B1
(45) Date of Patent: Aug. 13, 2002

(54) USE OF RILUZOLE OR ITS SALTS FOR THE PREVENTION AND TREATMENT OF ADRENOLEUKODYSTROPHY

(75) Inventors: Patrick Aubourg, Boulogne-Billancourt; Michel Dib, Paris; Jean-Marie Stutzmann, Villecresnes, all of (FR)

(73) Assignees: Aventis Pharm SA, Antony Cedex; Institut Nationale de la Sante et de la Recherche Medicale (INSERM), Paris, both of (FR)

( * ) Notice: Subject to any disclaimer, the term of this patent is extended or adjusted under 35 U.S.C. 154(b) by 0 days.

(21) Appl. No.: 09/873,270

(22) Filed: Jun. 5, 2001

Related U.S. Application Data

(60) Provisional application No. 60/216,159, filed on Jul. 3, 2000.

(30) Foreign Application Priority Data

Jun. 5, 2000 (FR) .............................................. 00 07162

(51) Int. Cl.$^7$ ............................................. A61K 31/428
(52) U.S. Cl. ......................................................... 514/367
(58) Field of Search ........................................... 514/367

(56) References Cited

FOREIGN PATENT DOCUMENTS

| EP | 0 305 276 | * | 3/1989 |
| WO | WO 99 51097 | | 10/1999 |

OTHER PUBLICATIONS

Vogels et al., Neurology, 52/6, (1275–1277) (1999).*
Singh I., et al., "Lovastatin therapy for X–linked adrenoleukodystrophy ($X_{ALD}$).", *Journal of Neurochemistry*, 72 p. S19 (1999).
Rilutek Press Release: Dec. 12, 1995.

* cited by examiner

*Primary Examiner*—Phyllis G. Spivack
(74) *Attorney, Agent, or Firm*—Finnegan, Henderson, Farabow, Garrett & Dunner LLP

(57) ABSTRACT

The present invention relates to the use of riluzole or one of its pharmaceutically acceptable salts for the prevention and treatment of adrenoleukodystrophy.

19 Claims, No Drawings

USE OF RILUZOLE OR ITS SALTS FOR THE PREVENTION AND TREATMENT OF ADRENOLEUKODYSTROPHY

This application claims priority benefit of French Application No. FR 00 07162, filed Jun. 5, 2000, and U.S. Provisional Application No. 60/216,159, filed Jul. 3, 2000; the contents of which are expressly incorporated by reference herein.

The present invention relates to the use of riluzole or one of its pharmaceutically acceptable salts for the prevention and treatment of adrenoleukodystrophy.

BACKGROUND OF THE INVENTION

Riluzole (2-amino-6-trifluoromethoxy-benzothiazole) is marketed for the treatment of amyotrophic lateral sclerosis (RILUTEK®). This compound is also useful as an anticonvulsant, an anxiolytic, and a hypnotic (EP 50551), in the treatment of schizophrenia (EP 305276), in the treatment of sleep disorders and of depression (EP 305277), in the treatment of cerebrovascular disorders and as an anaesthetic (EP 282971), in the treatment of spinal, cranial and craniospinal traumas (WO 94/13288), as a radio restorative (WO 94/15600), in the treatment of Parkinson's disease (WO 94/15601), in the treatment of neuro-AIDS (WO 94/20103), and in the treatment of mitochondrial diseases (WO 95/19170).

X-linked adrenoleukodystrophy (ADL) is the most frequent of the genetic diseases of myelin, which is characterized by progressive demyelination of the central nervous system, an adrenal insufficiency and a moderate accumulation (3 to 5 times) of very long chain fatty acids (VLCFA) in most tissues, including the brain and the spinal cord. This accumulation of VLCFA results from a deficiency in their $\beta$-oxidation in the peroxisome.

The mechanisms which lead in ALD to demyelination and loss of oligodendrocytes are still not well understood. One of the possibilities is that the accumulation of VLCFAs leads to a destabilization of the myelinic membranes or to a dysfunctioning of the receptors situated at the surface of the oligodendrocytes, making the receptors more sensitive to signals for programmed cell death (apoptosis). The death of the oligodendrocytes could also result from the production of cytokines (in particular TNF-$\alpha$ by the activated macrophages, which are present in the cerebral inflammatory lesions in ALD.

In a study of the fragmentation of the DNA, by the TUNEL method and by the expression of caspase-3, 50% of the oligodendrocytes of ALD patients, brains exhibit signs of cell death by apoptosis. Further, the intensity of the apoptotic phenomena is correlated with the intensity of the demyelination.

Death of the oligodendrocytes by apoptosis was recently demonstrated in several other murine models of genetic disease of myelin: in the twitcher mouse (model of Krabbe's disease), and in various models such as jimpy mouse, msd mouse, and md rat (models deficient in proteolipid protein, PLP).

SUMMARY OF THE INVENTION

It has now been found that at least one active ingredient chosen from riluzole and its pharmaceutically acceptable salts reduces oligodendrocyte death from apoptosis induced by kainite. Thus, in one embodiment, the invention provides a method of treating adrenoleukodystrophy comprising administration of at least one active ingredient chosen from riluzole and its pharmaceutically acceptable salts.

The invention also provides a method of preventing adrenoleukodystrophy comprising administration of at least one active ingredient chosen from riluzole and its pharmaceutically acceptable salts.

In another embodiment, the invention relates to a method of preparing a medicament useful for the treatment of adrenoleukodystrophy comprising adding at least one active ingredient chosen from riluzole and its pharmaceutically acceptable salts, to the medicament.

The invention also relates to a method of preparing a medicament useful for the prevention of adrenoleukodystrophy comprising adding at least one active ingredient chosen from riluzole and its pharmaceutically acceptable salts, to the medicament.

The invention further relates to a method of preparing a medicament useful in the treatment of adrenoleukodystrophy comprising mixing at least one active ingredient chosen from riluzole and its pharmaceutically acceptable salts, with at least one compatible and pharmaceutically acceptable diluent and/or adjuvant.

The invention further relates to a method of preparing a medicament useful in the prevention of adrenoleukodystrophy comprising mixing at least one active ingredient chosen from riluzole and its pharmaceutically acceptable salts, with at least one compatible and pharmaceutically acceptable diluent and/or adjuvant.

In another embodiment, the invention relates to the method of treating adrenoleukodystrophy in a patient, comprising administering an effective amount of at least one active ingredient chosen from riluzole and its pharmaceutically acceptable salts to the patient.

The invention also relates to the method of preventing adrenoleukodystrophy in a patient, comprising administering an effective amount of at least one active ingredient chosen from riluzole and its pharmaceutically acceptable salts to the patient.

It is to be understood that both the foregoing general description and the following detailed description are exemplary and explanatory only and are not restrictive of the invention as claimed. Reference will now be made in detail to exemplary embodiments of the present invention.

DETAILED DESCRIPTION OF THE INVENTION

Pharmaceutically acceptable salts of riluzole include, but are not limited to, addition salts with inorganic acids such as, for example, hydrochloride, sulfate, nitrate, or phosphate, or with organic acids such as acetate, propionate, succinate, oxalate, benzoate, fumarate, maleate, methane-sulfonate, isethionate, theophyllineacetate, salicylate, phenolphthalinate, or methylene-bis-$\beta$-oxy-naphthoate, and substitution derivatives of these derivatives.

The medicaments of the invention may comprise, for example, at least one riluzole compound, chosen from riluzole in free form, and riluzole in the form of an addition salt with a pharmaceutically acceptable acid. The at least one riluzole compound may be in a pure state or in the form of a composition in which it is combined with any other pharmaceutically compatible product, which may be inert or physiologically active. The medicaments according to the invention may, for example, be used by at least one of the oral, parenteral and rectal routes.

Solid compositions for oral administration may be chosen from, for example, tablets, pills, powders, gelatin capsules, cachets, and granules. In one embodiment, these compositions comprise the active ingredient according to the invention mixed with at least one inert diluent such as, for example, starch, cellulose, sucrose, lactose, and silica, under an argon stream. These compositions may also comprise substances other than diluents, such as, for example at least one of a lubricant, such as magnesium stearate or talc, a coloring, a coating (sugar-coated tablets), and a glaze.

Liquid compositions for oral administration may be chosen from, for example, pharmaceutically acceptable solutions, suspensions, emulsions, syrups, and elixirs. The liquid composition may further comprise inert diluents such as water, ethanol, glycerol, vegetable oils, and paraffin oil. These compositions may also comprise substances other than diluents, chosen from, for example wetting, sweetening, thickening, flavoring, and stabilizing products.

Sterile compositions for parenteral administration may be chosen from, for example, aqueous solutions, nonaqueous solutions, suspensions, and emulsions. As a solvent or vehicle, water, propylene glycol, polyethylene glycol, vegetable oils (such as olive oil), injectable organic esters (such as ethyl oleate), and other suitable organic solvents may be used. These compositions may also contain adjuvants, including, for example, wetting agents, isotonizing agents, emulsifying agents, dispersing agents, and stabilizing agents.

The sterilization may be carried out in several ways, including, but not limited to, aseptisizing filtration, incorporating sterilizing agents into the composition, irradiation and heating. Sterile compositions can also be prepared in the form of sterile solid compositions which may be dissolved at the time of use in sterile water or in any other injectable sterile medium.

The compositions for rectal administration may be, for example, suppositories or rectal capsules which may comprise, in addition to the at least one active ingredient, at least one excipient such as cocoa butter, semisynthetic glycerides, or polyethylene glycols.

The dose(s) of the active ingredient depends on the desired effect, on the duration of the treatment, and on the route of administration used. In one embodiment, the dose ranges from 50 mg and 400 mg per day by the oral route for an adult, with unit doses ranging from 25 mg to 200 mg of active substance.

In general, the doctor will determine the appropriate dosage according to the age, weight and all the other factors specific to the subject to be treated.

The invention will be illustrated by, but is not intended to be limited to, the following example.

EXAMPLE 1

The protocol used was the following:
Cultures enriched with oligodendrocytes

Oligodendrocytes were obtained from primary glial cultures of spinal cords according to the slightly modified method described by Saneto et al. (Neurochemistry, a Practical Approach, IRL Press, oxford-Washington, D.C., p 27–63 (1987)). Spinal cords from 1-day old Wistar rats were dissected under sterile conditions and separated from the meninges. Five to ten spinal cords were transferred into PBS (phosphate-buffered saline: NaCl 137 mM, KCl 2.68 mM, $Na_2HPO_4$ 6.45 mM, $KH_2PO_4$ 1.47 mM) to which 0.25% of trypsin was added. The enzymatic treatment was stopped by addition of Dubelco's modified Eagle's medium (DMEM) to which 10% of fetal bovine serum was added (FBS). Another dissolution step was carried out by means of a 1 ml pipette, and the cell suspension was filtered. The cells were collected by centrifugation and plated at a density of $1.5-2 \times 10^6$ cells/25 $cm^2$ of culture medium in Dubelco's modified Eagle's medium (DMEM) to which 10% of fetal bovine serum was added. After 3 days in vitro, the cultures were fed daily. When a visible monolayer was obtained, the cultures were stirred for 2 hours at 37° C. at 250 rpm, the culture medium was removed, and the flasks were again stirred for 22 hours. The cell-containing medium was incubated at 37° C. in petri dishes for 1 hour in order for the microglia to become attached to the plastic. The oligodendrocytes were collected by centrifugation, plated at a density of $1.6 \times 10^6/cm^2$ and maintained in DMEM containing 10% FBS for 1 or 2 days. The medium was then replaced with L15 medium to which sodium bicarbonate (22 mM), conalbumin (0.1 mg/ml), putrescine (0.1 mM), insulin (5 $\mu$g/ml), sodium selenite (31 nM), glucose (20 mM), progesterone (21 nM), penicillin (100 IU/ml), streptomycin (100 $\mu$g/ml), and horse serum (2%) were added. The oligodendrocytes rapidly differentiated within 24 to 48 hours into a mature and immature phenotype. These cultures showed a purity of about 95%, as determined by immunoreactivity to galactocerebroside-C (Gal-C) and to glial fibrillary acidic protein (GFAP).

Kainate in solution in PBS at various concentrations (0.01 mM to 1 mM), riluzole in solution in NaCl at 0.9% and HCl at 0.001 N, at various concentrations (0.01 mM to 10 mM) or solvent were then added to these cultures. After 48 hours, measured from the start of treatment, the living oligodendrocytes were counted.

Counting of the cells

The cells immunoreactive for Gal-C and exhibiting branched processes longer than the diameters of 2 cells were considered overall as immature or mature oligodendrocytes. The number of Gal-C (+) oligo-dendrocytes were divided for 2 separate counts of the labeled cells in at least 12 fields of 0.63 $mm^2$ under a 400X microscope. The values were expressed as the number of cells per $cm^2$ or as the percentage of the control.

The statistical analyses were carried out using the Student's test (t-test).

The results obtained were as follows:

The cultures of oligodendrocytes were exposed to concentrations of 0.1 to 1 mM kainate for 48 hours.

|  | Number of oligodendrocytes % relative to the control ± standard deviation |
|---|---|
| Solvent alone | 100 ± 17.4 |
| Kainate |  |
| 0.01 mM | 108.2 ± 25.2 |
| 0.1 mM | 76.3 ± 27.9 |
| 0.5 mM | 25.3 ± 9.3 |
| 1 mM | 22.9 ± 7.1 |

These results showed that kainate at doses of from about 0.1 mM to about 1 mM strongly induced death of the oligodendrocytes through apoptosis.

Test 2

Investigation of the toxic effect of riluzole alone on cultures of oligodendrocytes The cultures of oligodendrocytes were exposed to concentrations of 0.01 mM to 10 mM riluzole for 48 hours.

|  | Number of oligodendrocytes % relative to the control ± standard deviation |
| --- | --- |
| Solvent | 100 ± 8.2 |
| Riluzole |  |
| 0.01 mM | 99.6 ± 15.7 |
| 0.1 mM | 94.3 ± 17.3 |
| 1 mM | 107.1 ± 9.5 |
| 10 mM | 86.9 ± 16 |

These results demonstrated that riluzole at the doses of 0.01 mM to 10 mM had no toxic effect on the survival of the oligodendrocytes, and that at the dose of about 10 mM, a slightly toxic effect was observed.

Test 3

Protective effect of riluzole on oligocytes death induced by kainate

The oligodendrocyte cultures were exposed to kainate at a dose of 1 mM and to riluzole at doses of from about 0.01 mM to about 10 mM.

|  | Number of oligodendrocytes % relative to the control ± standard deviation |
| --- | --- |
| Kainate 1000 | 22.9 ± 7.1 |
| Kainate 1 mM + riluzole 0.01 mM | 48.7 ± 7 |
| Kainate 1 mM + riluzole 0.1 mM | 65.2 ± 9.2 |
| Kainate 1 mM + riluzole 1 mM | 69.4 ± 12 |
| Kainate 1 mM + riluzole 10 mM | 56.3 ± 6.9 |

These results demonstrated that riluzole reduced oligodendrocyte death from apoptosis induced by kainate, even at the dose where a slight toxic effect of riluzole alone was observed. Thus, riluzole may be used in the prevention and treatment of adrenoleukodystrophy.

EXAMPLE 2

The following examples illustrate medicaments according to the invention:

Example A

Tablets containing a 50 mg dose of at least one active ingredient having the following composition are prepared according to standard techniques:

| Riluzole | 50 mg |
| --- | --- |
| Mannitol | 64 mg |
| Microcrystalline cellulose | 50 mg |
| Polyvidone excipient | 12 mg |
| Sodium carboxymethylstarch | 16 mg |
| Talc | 4 mg |
| Magnesium stearate | 2 mg |
| Anhydrous colloidal silica | 2 mg |
| Mixture of methylhydroxypropylcellulose, polyethylene glycol 6000, titanium dioxide (72–3.5–24.5) qs 1 finished film-coated tablet weighing | 245 mg |

Example B

Gelatin capsules containing a 50 mg dose of at least one active ingredient having the following composition are prepared according to standard techniques:

| Riluzole | 50 mg |
| --- | --- |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example C

An injectable solution containing 10 mg of active product having the following composition is prepared:

| Riluzole | 10 mg |
| --- | --- |
| Benzoic acid | 80 mg |
| Benzyl alcohol | 0.06 cm$^3$ |
| Sodium benzoate | 80 mg |
| Ethanol at 95% | 0.4 cm$^3$ |
| Sodium hydroxide | 24 mg |
| Propylene glycol | 1.6 cm$^3$ |
| Water | qs 4 cm$^3$ |

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method of treating adrenoleukodystrophy in a patient, comprising administering from 25 mg to 200 mg of at least one active ingredient chosen from riluzole and its pharmaceutically acceptable salts to the patient.

2. A method of treating adrenoleukodystrophy comprising administration of a composition comprising at least one active ingredient chosen from riluzole and its pharmaceutically acceptable salts.

3. The method of claim 1, wherein said pharmaceutically acceptable salt is chosen from addition salts with inorganic acids.

4. The method of claim 3, wherein said addition salt is chosen from hydrochloride, sulfate, nitrate, and phosphate.

5. The method of claim 1, wherein said pharmaceutically acceptable salt is chosen from addition salts with organic acids.

6. The method of claim 5, wherein said addition salt is chosen from acetate, propionate, succinate, oxalate, benzoate, fumarate, maleate, methane-sulfonate, isethionate, theophyllineacetate, salicylate, phenolphthalinate, and methylene-bis-β-oxy-naphthoate.

7. The method of claim 1, wherein said administration is chosen from at least one of oral administration, parenteral administration, and rectal administration.

8. The method of claim 1, wherein said composition is a solid composition.

9. The method of claim 8, wherein said solid composition is chosen from tablets, pills, powders, gelatin capsules, cachets, and granules.

10. The method of claim 9, wherein said solid composition further comprises at least one inert diluent chosen from starch, cellulose, sucrose, lactose and silica.

11. The method of claim 1, wherein said composition is a liquid composition.

12. The method of claim 11, wherein said liquid composition is chosen from a pharmaceutically acceptable solution, a pharmaceutically acceptable suspension, a pharmaceutically acceptable emulsion, a pharmaceutically acceptable syrup, and a pharmaceutically acceptable elixir.

13. The method of claim 12, wherein said liquid composition further comprises at least one inert diluent chosen from water, ethanol, glycerol, vegetable oil, and paraffin oil.

14. The method of claim 1, wherein said composition is a sterile composition.

15. The method of claim 14, wherein said sterile composition is chosen from an aqueous solution, a nonaqueous solution, a suspension, and an emulsion.

16. The method of claim 1, wherein said sterile composition further comprises at least one solvent or vehicle chosen from water, propylene glycol, polyethylene glycol, vegetable oil, and an injectable organic ester.

17. The method of claim 1, wherein said composition is a rectal administration composition chosen from a suppository and a rectal capsule.

18. A method of preventing adrenoleukodystrophy in a patient, comprising administering from 25 mg to 200 mg of at least one active ingredient chosen from riluzole and its pharmaceutically acceptable salts to the patient.

19. A method of preventing adrenoleukodystrophy comprising administration of at least one active ingredient chosen from riluzole and its pharmaceutically acceptable salts.

* * * * *